(12) United States Patent
Koura

(10) Patent No.: US 11,872,364 B2
(45) Date of Patent: Jan. 16, 2024

(54) FLUID-DELIVERY SYSTEM, DEVICE, AND ADAPTER FOR DELIVERING FLUID TO TISSUE

(71) Applicant: Dravid Koura, Singapore (SG)

(72) Inventor: Dravid Koura, Singapore (SG)

( * ) Notice: Subject to any disclaimer, the term of this patent is extended or adjusted under 35 U.S.C. 154(b) by 961 days.

(21) Appl. No.: 16/660,445

(22) Filed: Oct. 22, 2019

(65) Prior Publication Data

US 2020/0121865 A1    Apr. 23, 2020

Related U.S. Application Data

(60) Provisional application No. 62/749,297, filed on Oct. 23, 2018.

(51) Int. Cl.
| | |
|---|---|
| *A61M 3/02* | (2006.01) |
| *A61M 5/34* | (2006.01) |
| *A61M 39/10* | (2006.01) |
| *A61M 5/31* | (2006.01) |

(52) U.S. Cl.
CPC ........ *A61M 3/0237* (2013.01); *A61M 3/0201* (2021.05); *A61M 5/3134* (2013.01);
(Continued)

(58) Field of Classification Search
CPC .... A61M 5/3134; A61M 5/345; A61M 5/178; A61M 5/34; A61M 5/31515; A61M 5/24; A61M 39/1011; A61M 2039/1033; A61M 3/0279; A61M 2005/2403; A61M 2005/2407; A61M 2005/2437; A61M 2005/2485; A61M 2005/2492; A61M 2005/244; A61M 2005/3128; A61M 2005/5046; A61M 5/28; A61M 39/10; A61M 2039/1077; A61M 2005/3139; A61M 5/142; A61M 5/14216;
(Continued)

(56) References Cited

U.S. PATENT DOCUMENTS 3,700,215 A * 10/1972 Hardman ................ B01F 35/71
366/268
4,808,169 A * 2/1989 Haber ...................... A61M 5/24
604/196
(Continued)

*Primary Examiner* — Emily L Schmidt
*Assistant Examiner* — Alexandra Lalonde
(74) *Attorney, Agent, or Firm* — Williams Intellectual Property; Timothy Snyder

(57) ABSTRACT

A fluid-delivery system, a fluid-delivery device, and an adapter are described herein for applying fluid to tissue. The adapter generally includes a proximal portion and a distal portion. The proximal portion includes a grasping handle to be grasped by a grasping instrument having a pair of jaws, and a collar surrounding the grasping handle to increase a grip on the pair of jaws. The distal portion is adapted to connect with the fluid-delivery device. The fluid-delivery device generally includes a tip to apply the fluid to the tissue, a tip saturator to supply the tip with the fluid, a flow regulator to control fluid flow to the tip saturator, and a fluid housing to contain the fluid which is appliable to the tissue. The fluid-delivery system includes the adapter connected with the fluid-delivery device. The fluid-delivery system is particularly advantageous for marking tissues during endoscopic surgical procedures.

19 Claims, 10 Drawing Sheets

(52) U.S. Cl.
CPC ........ *A61M 5/345* (2013.01); *A61M 39/1011*
(2013.01); *A61M 2039/1033* (2013.01)

(58) Field of Classification Search
CPC . A61M 5/1422; A61M 5/14212; A61B 10/06;
A61B 10/04; A61B 17/29; A61B 1/015;
A61B 2017/0046; A61B 2017/00486;
A61B 17/00491; A61B 17/3478; A61B
17/88802; A61B 34/30; A61B 2034/301;
A61B 17/3203; A61B 2218/001; A61B
2218/002; A61B 2218/007; A61B
2217/007; A61J 1/2096
See application file for complete search history.

(56) References Cited

U.S. PATENT DOCUMENTS

| | | | |
|---|---|---|---|
| 5,122,147 A | 6/1992 | Sewell | |
| 5,312,333 A | 5/1994 | Churinetz et al. | |
| 5,401,246 A * | 3/1995 | Mazur | A61M 5/322 604/110 |
| 6,296,608 B1 | 10/2001 | Daniels et al. | |
| 2005/0234507 A1 | 10/2005 | Geske et al. | |
| 2008/0082021 A1 | 4/2008 | Ichikawa et al. | |
| 2009/0217932 A1 | 9/2009 | Voegele | |
| 2010/0010472 A1* | 1/2010 | Moore | A61M 5/31596 604/88 |
| 2011/0060188 A1 | 3/2011 | Sharon et al. | |
| 2012/0226287 A1 | 9/2012 | Qadeer | |
| 2012/0271245 A1* | 10/2012 | Achan, Jr. | A61M 5/31511 604/236 |
| 2013/0079760 A1 | 3/2013 | Twomey et al. | |
| 2013/0338631 A1* | 12/2013 | Butlin | A61M 5/19 604/506 |
| 2014/0316336 A1* | 10/2014 | Hawasheen | A61M 5/502 604/110 |
| 2015/0183571 A1* | 7/2015 | Anderson | A61M 5/155 222/402.14 |
| 2015/0352293 A9 | 12/2015 | Cabrera Aquino et al. | |
| 2019/0038331 A1* | 2/2019 | Purdy | B01F 27/00 |

* cited by examiner

FLUID-DELIVERY SYSTEM, DEVICE, AND ADAPTER FOR DELIVERING FLUID TO TISSUE

BACKGROUND OF THE INVENTION

Endoscopic surgery is a highly effective minimally-invasive surgical technique. Conventional endoscopic techniques utilize miniature cameras and surgical tools that are fed through ports or other small openings (natural or otherwise) in a patient to perform various tasks (e.g., dissection, excision) on intracorporeal organs and tissues. One particular problem encountered during endoscopic surgery, however, is tissue movement, which can lead to disorientation during the procedure. A previously identified surgical site may need to be re-located in the event of movement, which can increase operating time and result in surgical error. Without a means to mark the tissue in the cavity, this movement is particularly difficult to monitor without additional medical imaging.

In other situations, such as during a training exercise or while demonstrating a particular endoscopic surgical procedure, it is common for the trainers to highlight or point-out specific organs, tissues, or features thereof. These tissue may be critical features that need to be avoided during the surgical operation (e.g., vital nerves and blood vessels). A method and/or device to aid in highlighting or marking these areas may be particularly beneficial during these training exercises.

In other surgical procedures, fluorescent dies or other contrasting agents may be used to highlight areas of normal and abnormal tissue. Many of these dies are injected intravenously or with the aid of x-ray or other medical imaging. These methods may be somewhat invasive and difficult to administer to specific target locations.

In general, any situation where direct visualization of a target location is limited, the delivery of a gas, fluid, gel or solid, to a target location is particularly difficult. Given the multitude of applications having such limitations, any device designed to provide such fluid-delivery should be non-expensive and easily adaptable to each of those different applications. Even more desirable, is a fluid-delivery device that is easily and quickly adaptable to a pre-existing tool. The pre-existing tool being able to attach with and operate the fluid-delivery device with minimal, if any, modification to the pre-existing tool. In addition, in a typical surgical area or surgical site there is positive pressure of up to 20 mmHg (average ~14 mmHg), so a fluid-delivery device must also be able to function under these pressures.

Thus, there exists a need for a fluid-delivery system, device, and adapter to adapt a pre-existing tool into a fluid-delivery device to deliver at least one of a gas, fluid, gel, or solid to mark a tissue, organ, or part thereof with a pigment, ink, or dye during an endoscopic surgical procedure. There is a further need for a system, device, and adapter to permit the pre-existing tool to deliver therapeutic or other agents to a tissue or organ. There may be an even further need for a system, device, and adapter to deliver fluid for non-medical applications wherein a gas, fluid, gel, or solid needs to be delivered to a target area under indirect visual conditions.

FIELD OF THE INVENTION

The present invention generally relates to a fluid-delivery device, and more particularly, to a fluid-delivery system, device, and adapter to adapt a grasping instrument into a fluid-delivery device for the delivery of fluids to tissues in visually restricted working areas or cavities.

SUMMARY

The general purpose of the fluid-delivery system, fluid-delivery device, and adapter described subsequently in greater detail, is to provide a fluid-delivery system which has many novel features that result in a system, device, and adapter which are not anticipated, rendered obvious, suggested, or even implied by prior art, either alone or in combination thereof.

A fluid-delivery system for applying fluid to tissue is described herein. The fluid-delivery system generally includes an adapter configured to connect with a grasping instrument and a fluid-delivery device configured to connect with the adapter and apply fluid to tissue. The adapter generally includes a proximal portion and a distal portion. The proximal portion has a grasping handle configured to be grasped by a grasping instrument having a pair of jaws. The distal portion is distal to the proximal portion and has a connection mechanism to connect with the fluid-delivery device. The fluid-delivery device generally includes a tip, a tip saturator, at least one flow regulator, and a fluid housing. The tip is at a distal end of the fluid-delivery device to apply fluid to tissue. The tip saturator is proximally adjacent to the tip to supply fluid to the tip. The at least one flow regulators are proximally adjacent to the tip saturator to regulate flow to the tip saturator. The fluid housing is proximal to the flow regulator and contains fluid appliable to tissue. The fluid-delivery device further includes a connection mechanism proximal to the fluid housing to connect with the connection mechanism on the adapter.

An adapter is described herein that is configured to connect with a grasping instrument and a fluid-delivery device. The adapter includes a proximal portion and a distal portion. The proximal portion includes a grasping handle and a collar positioned about at least a portion of the handle such that a pair of openings are formed between the handle and the collar. The handle is configured to be grasped by a grasping instrument having a pair of jaws. Each of said openings is configured to receive and encircle a jaw of the grasping instrument to further stabilize and secure the adapter to the grasping instrument. The distal portion is distal to the proximal portion and includes a first connection mechanism configured to connect with a fluid-delivery device.

A fluid-delivery device is described herein configured to connect with an adapter that connects with a grasping instrument. The fluid-delivery device generally includes a tip, a tip saturator, a flow regulator, and a fluid housing. The tip is at a distal end of the fluid-delivery device to apply fluid to tissue. The tip saturator is proximally adjacent to the tip to supply fluid to the tip. The at least one flow regulators are proximally adjacent to the tip saturator to regulate flow to the tip saturator. The fluid housing is proximal to the flow regulator and contains fluid appliable to tissue. The fluid-delivery device further includes a connection mechanism proximal to the fluid housing to connect with the connection mechanism on the adapter.

Objects of the present system, device, and adapter, along with various novel features that characterize the invention are particularly pointed out in the claims forming a part of this disclosure. For better understanding of the system, device, adapter and their operating advantages and specific objects attained by its uses, refer to the accompanying drawings and description.

BRIEF DESCRIPTION OF THE DRAWINGS

In the figures, identical structures, element or parts that appear in more than one figure are generally labeled with a same numeral in all the figures in which they appear. Dimensions of components and features shown in the figure are generally chosen for convenience and clarity of presentation and are not necessarily shown to scale. The figures are listed below.

FIGURES

Figure 1:
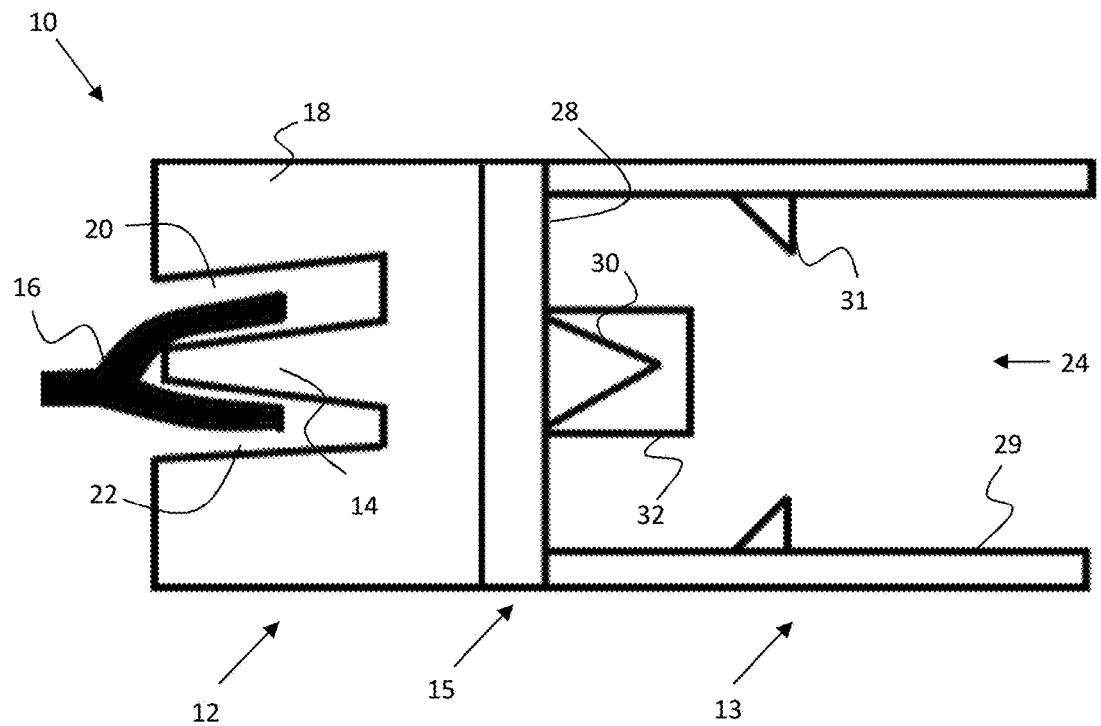

FIG. 1 is a longitudinal cross-sectional view of the adapter in accordance with embodiments of the invention.

Figure 2:
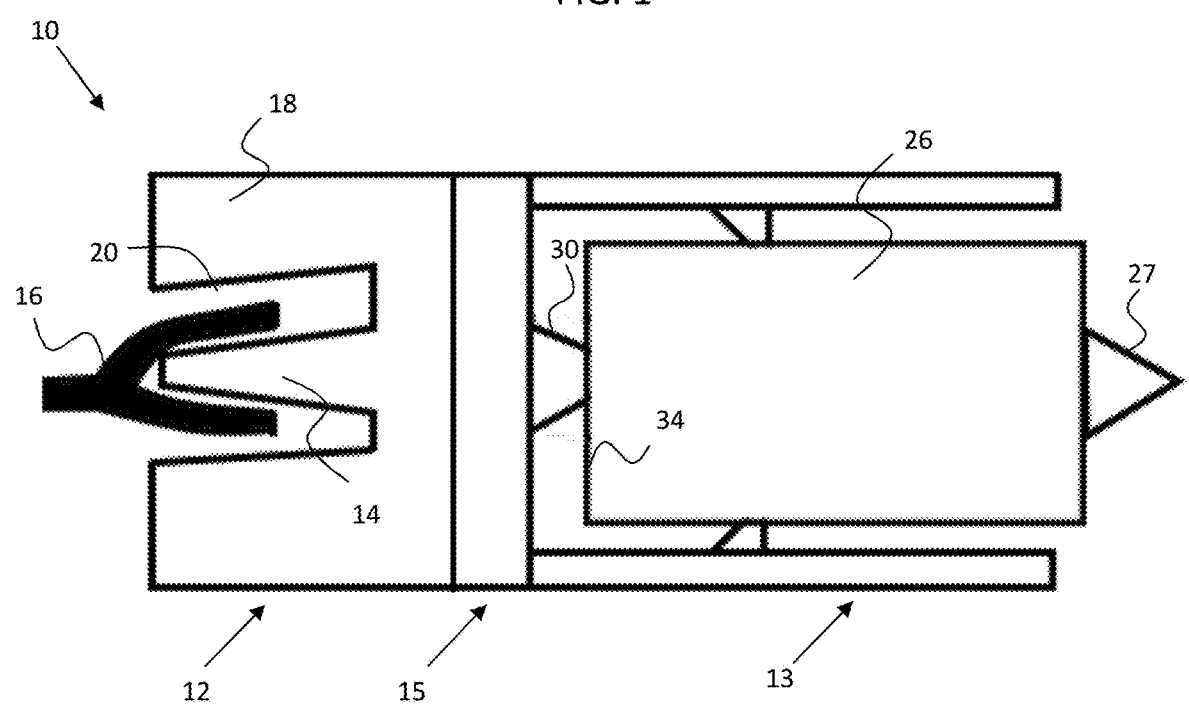

FIG. 2 is a longitudinal cross-sectional view of the adapter having a fluid-delivery device therein in accordance with embodiments of the invention.

Figure 3:
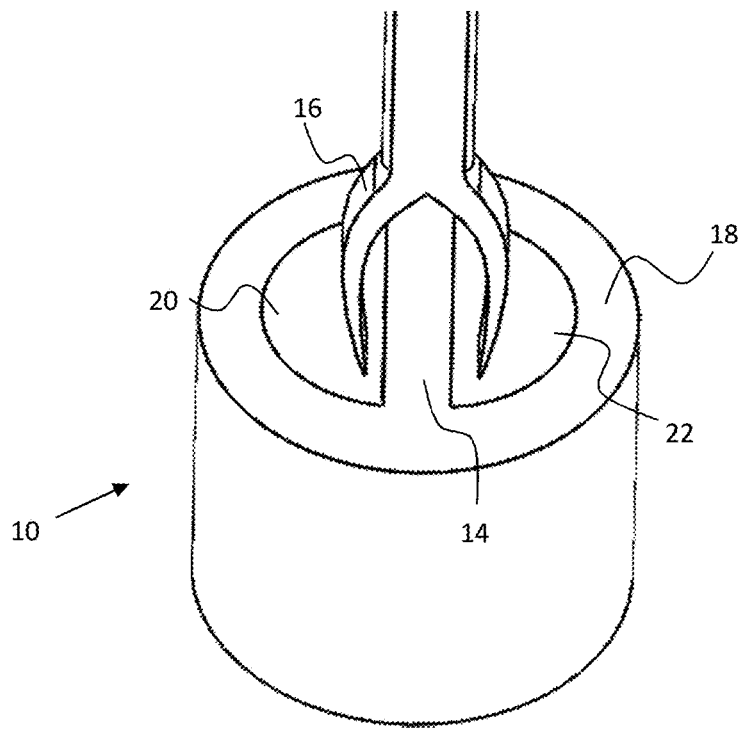

FIG. 3 is a picture of a pair of jaws grasping a handle of the adapter in accordance with embodiments of the invention.

Figure 4:
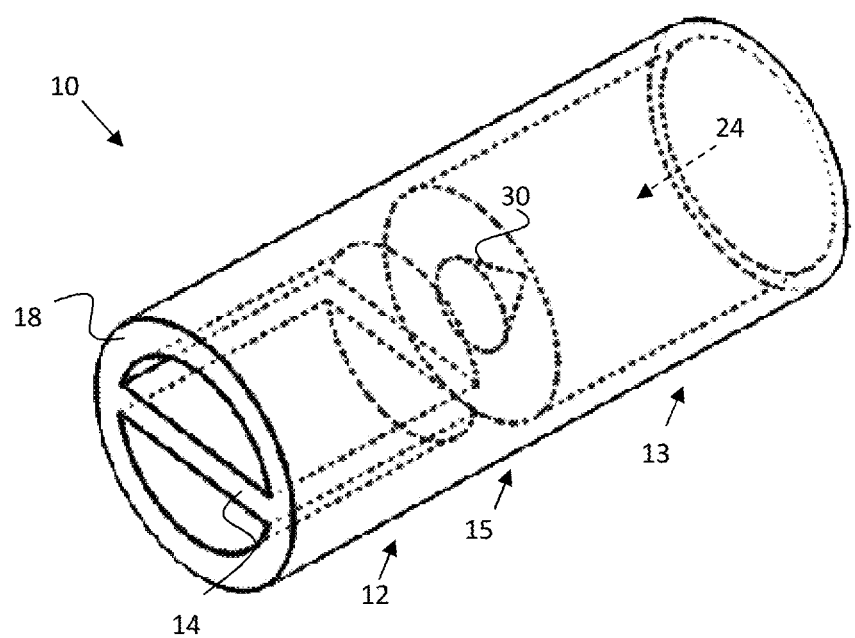

FIG. 4 is a perspective view of the adapter, where internal structures are shown with dotted lines in accordance with embodiments of the invention.

Figure 5:
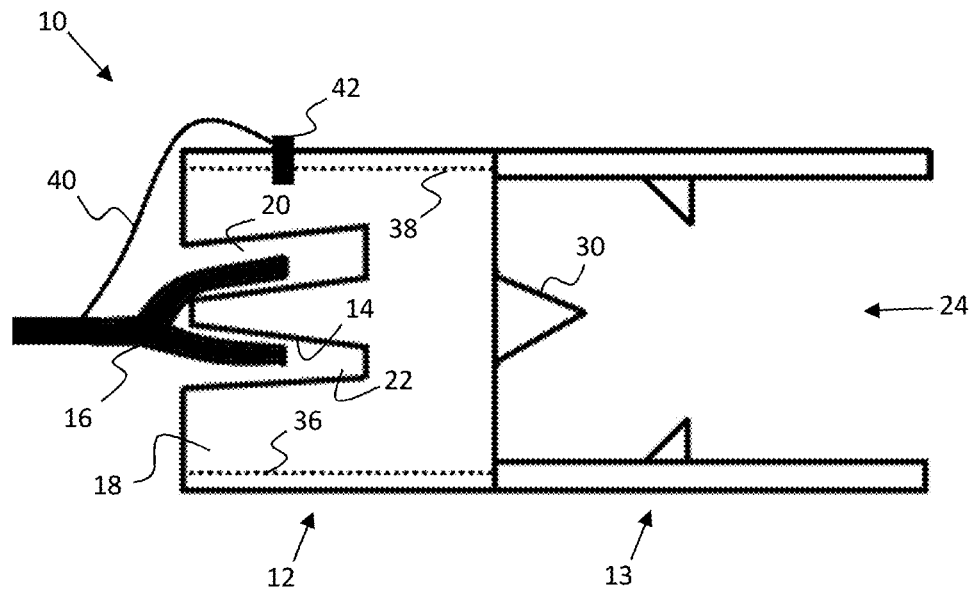

FIG. 5 depicts a longitudinal cross-sectional view of the adapter having a detaching mechanism and an anchoring mechanism in accordance with embodiments of the invention.

Figure 6:
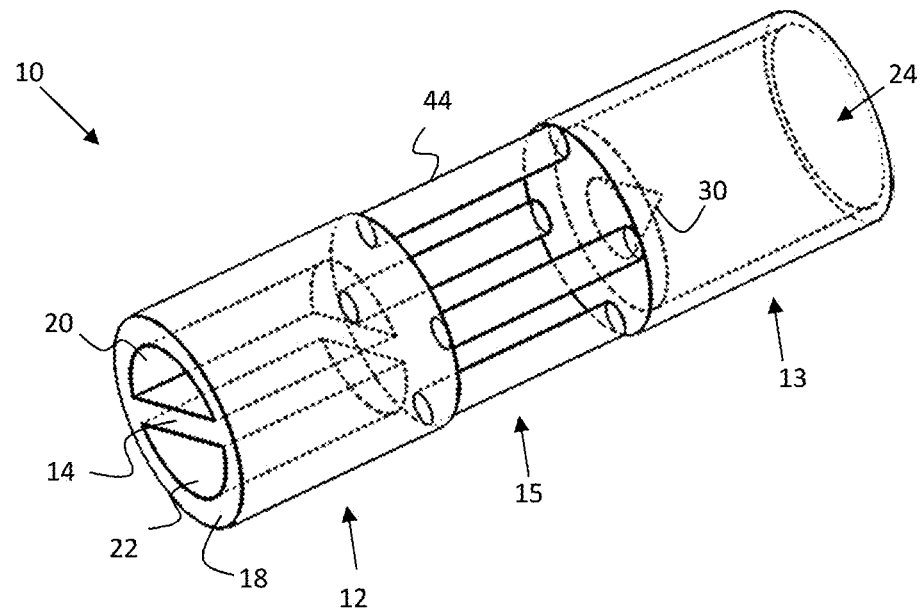

FIG. 6 depicts a perspective view of the adapter having malleable support structures in accordance with embodiments of the invention.

Figure 7:
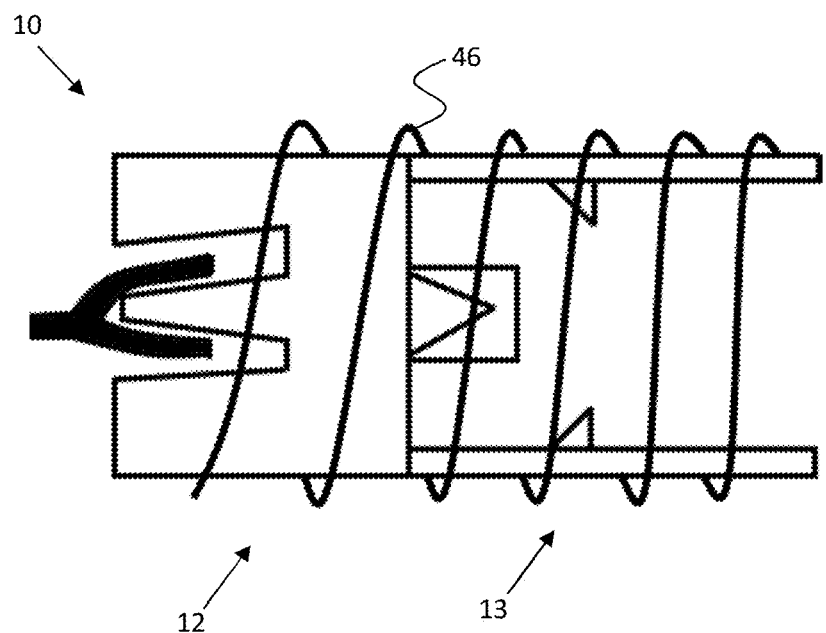

FIG. 7 depicts a side view of the adapter having a malleable spiral support structure in accordance with embodiments of the invention.

Figure 8:
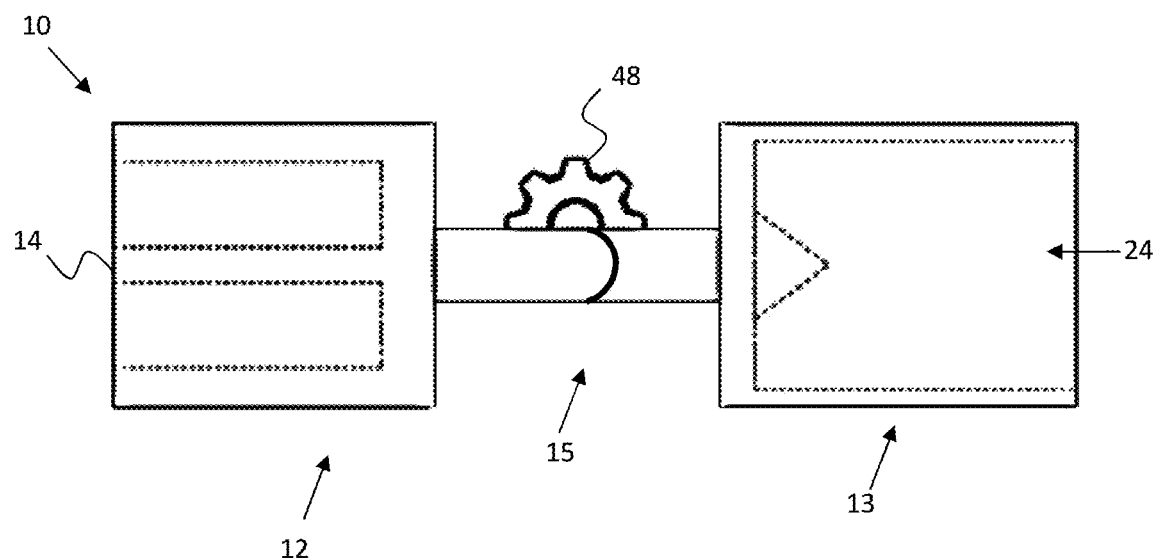

FIG. 8 depicts a side view of the adapter having a ratcheting hinge in accordance with embodiments of the invention.

Figure 9:
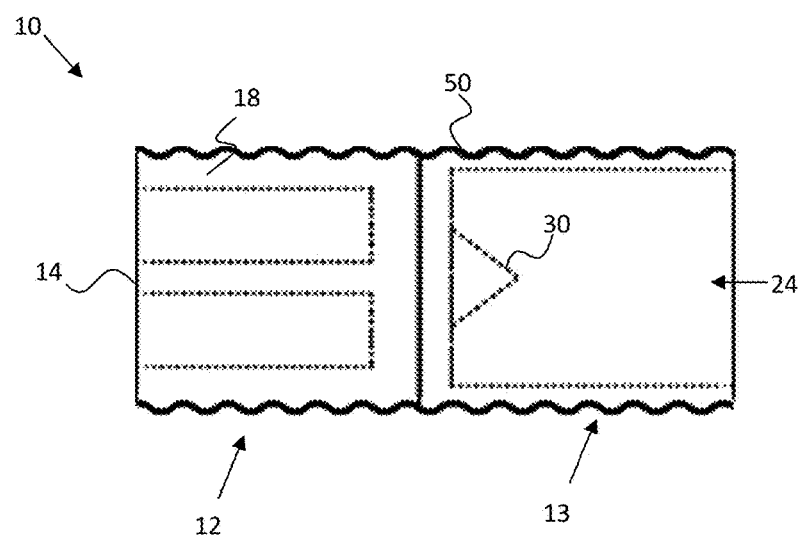

FIG. 9 depicts a side view of the adapter having corrugations in accordance with embodiments of the invention.

Figure 10:
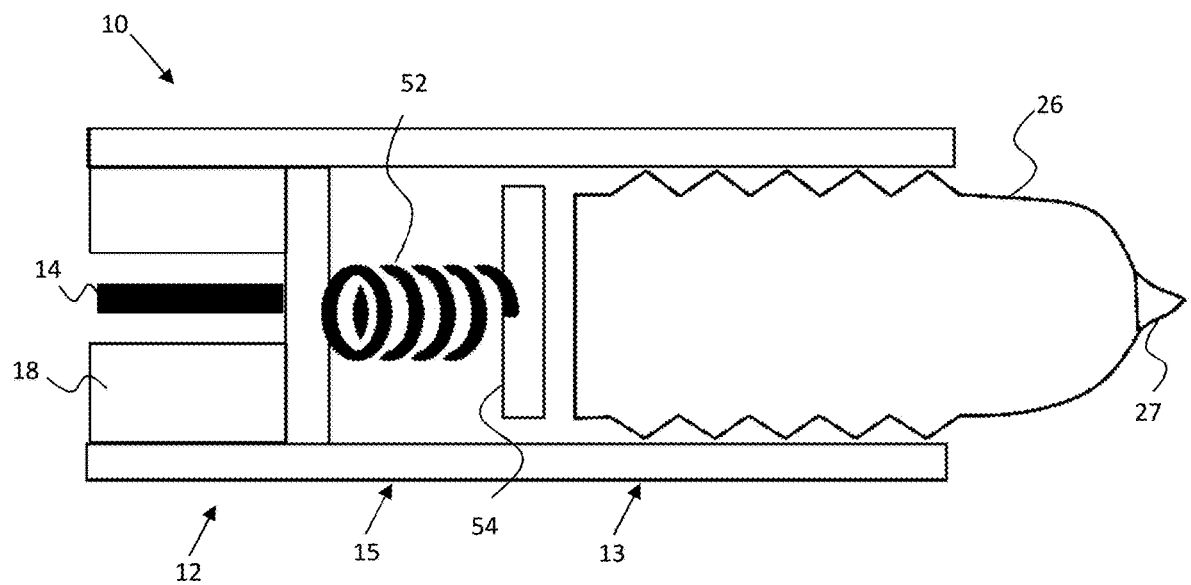

FIG. 10 depicts a side view of the adapter having a spring mechanism in accordance with embodiments of the invention.

Figure 11:
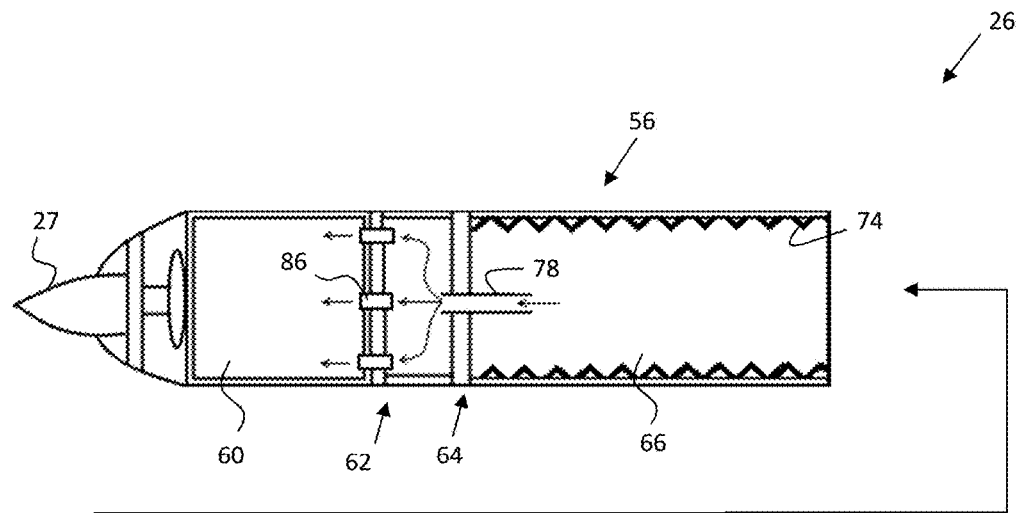
Figure 11:
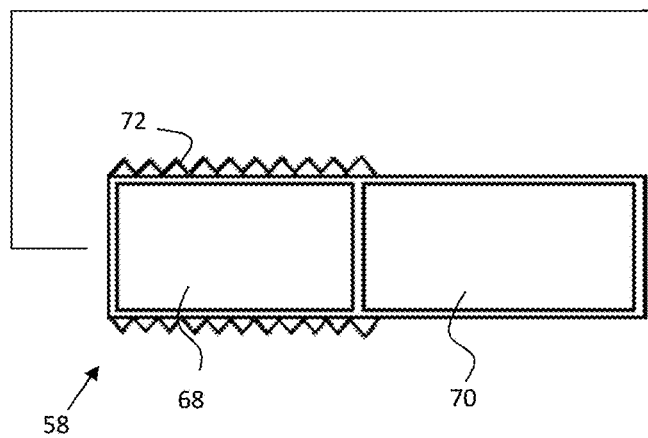

FIG. 11 depicts a longitudinal cross-sectional side view of a fluid-delivery device in accordance with embodiments of the invention.

Figure 12:
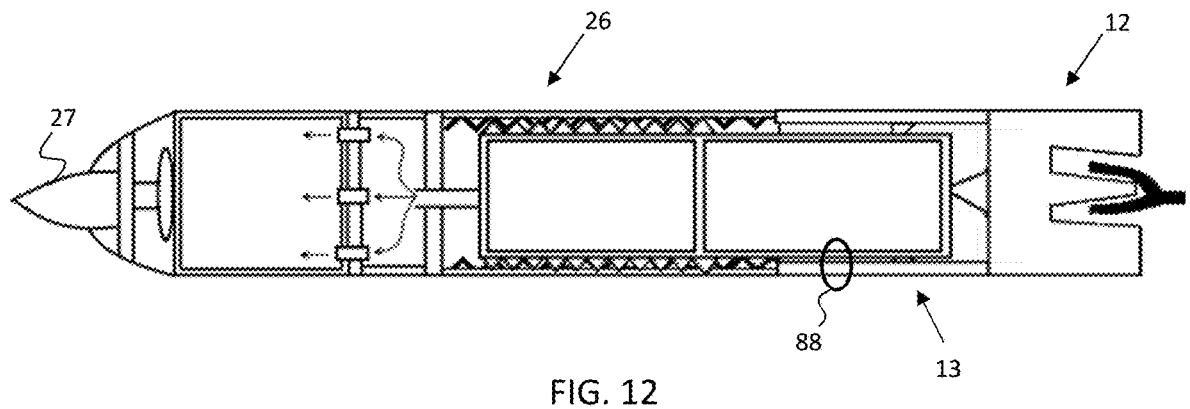

FIG. 12 depicts a longitudinal cross-sectional side view of the fluid-delivery device connected with the adapter in accordance with embodiments of the invention.

Figure 13A:
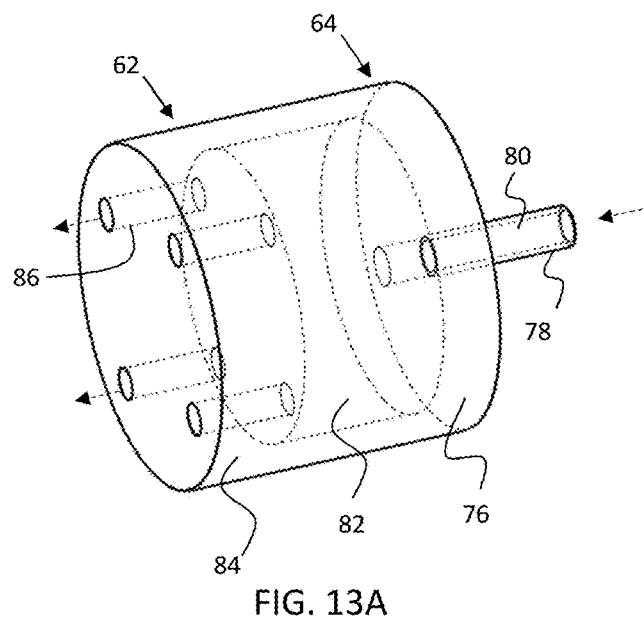
Figure 13B:
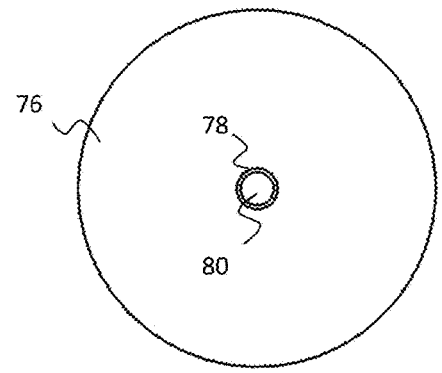
Figure 13C:
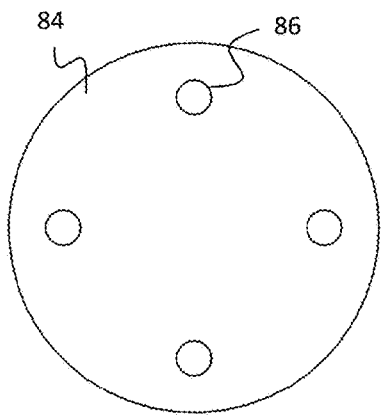
Figure 13D:
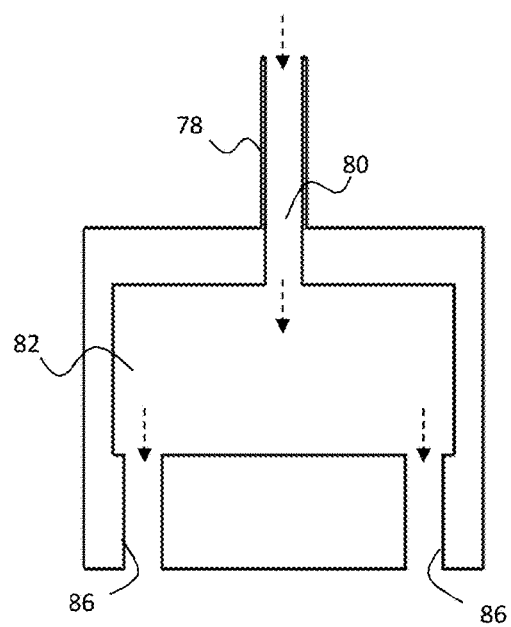

FIGS. 13A to 13D depict a primary flow regulator and a secondary flow regulator of the fluid-delivery device in accordance with embodiments of the invention, where FIG. 13A is a perspective view thereof, FIG. 13B is a proximal view thereof, FIG. 13C is a distal view thereof, and FIG. 13D is a cross-sectional view thereof.

Figure 14A:
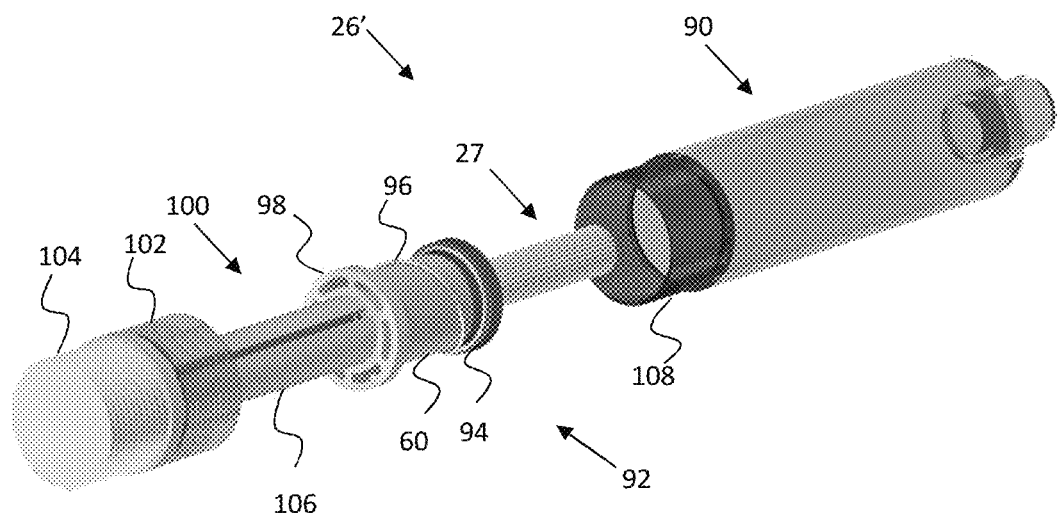
Figure 14B:
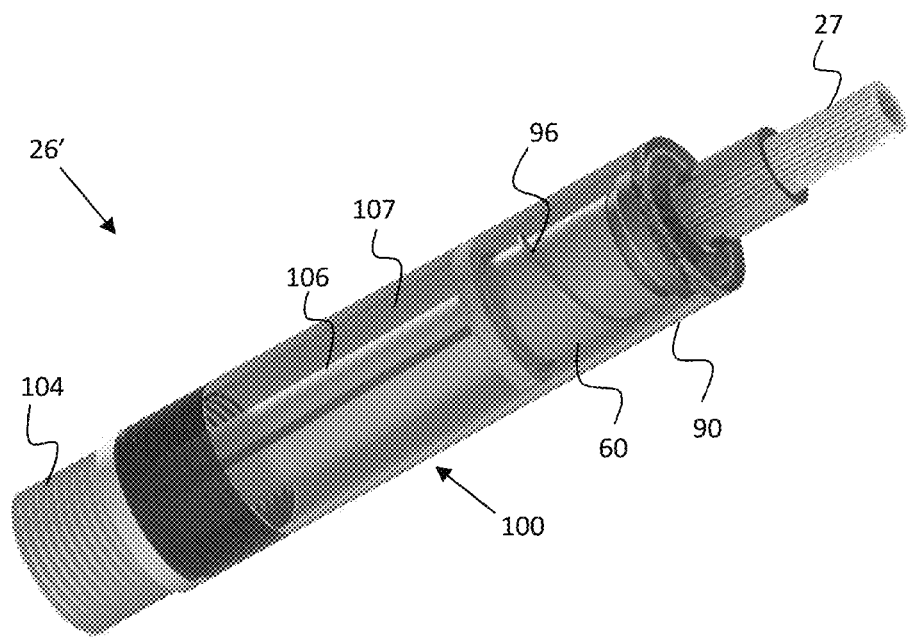

FIGS. 14A and 14B depict an embodiment of a fluid-delivery device having an incorporated fluid housing, where FIG. 14A is an exploded view thereof, and FIG. 14B is an assembled view thereof.

Figure 15A:
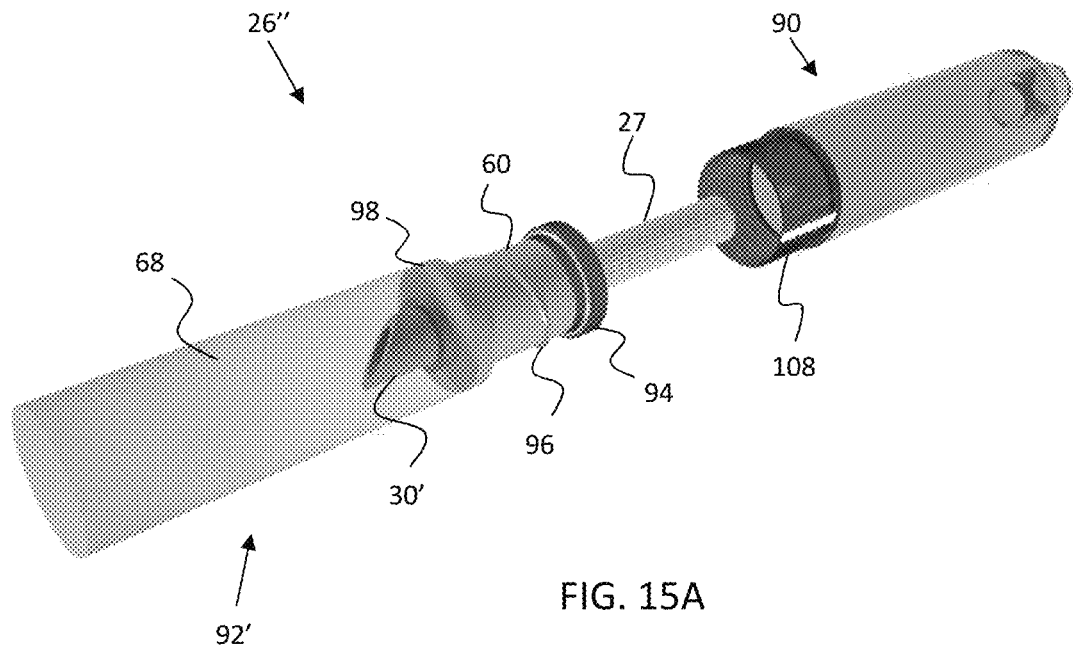
Figure 15B:
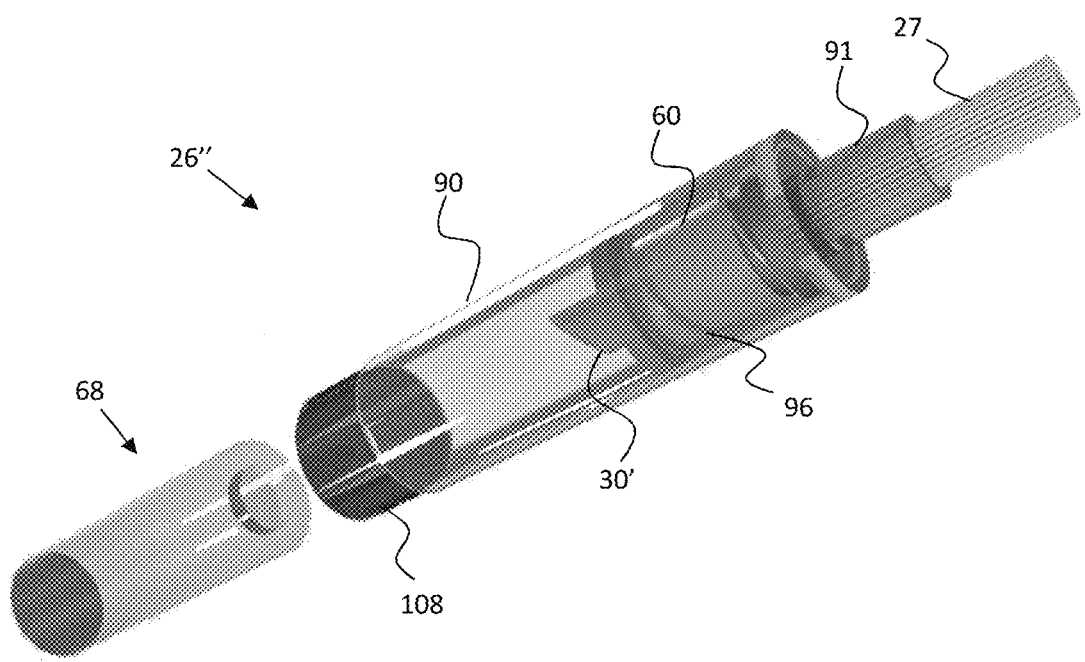

FIGS. 15A and 15B depict an embodiment of a fluid-delivery device having a cartridge fluid housing, where FIG. 15A is an exploded view thereof, and FIG. 15B is an assembled view thereof with the cartridge outside the fluid-delivery device.

Figure 16:
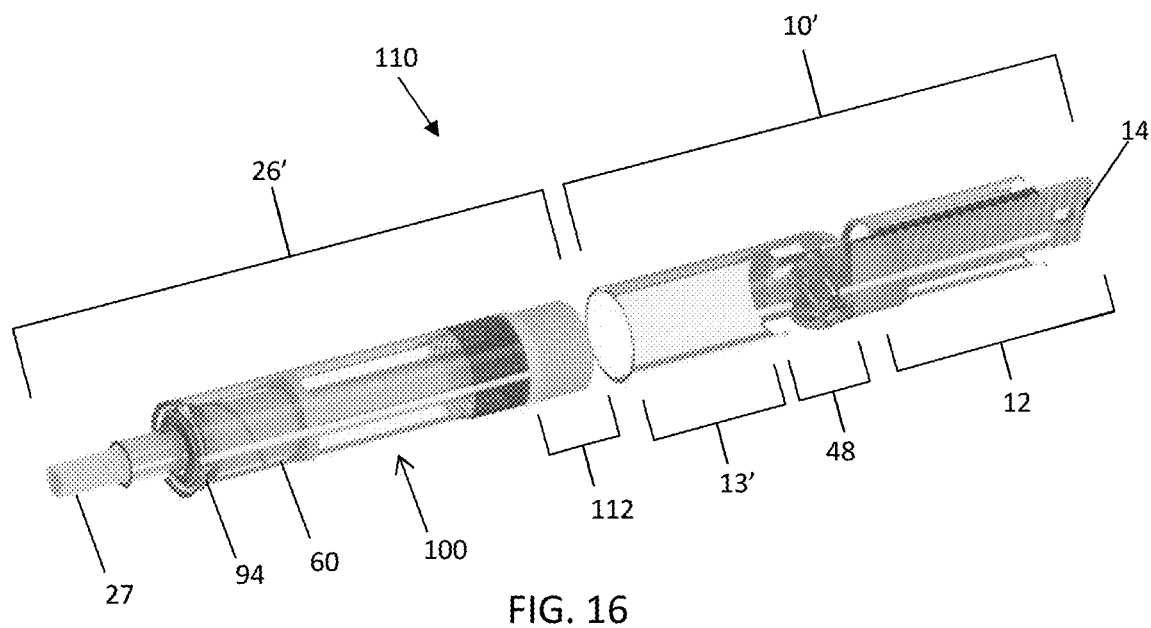

FIG. 16 depicts an embodiment of a fluid-delivery system having the fluid-delivery device of FIGS. 14A and 14B connected to an adapter.

Figure 17:
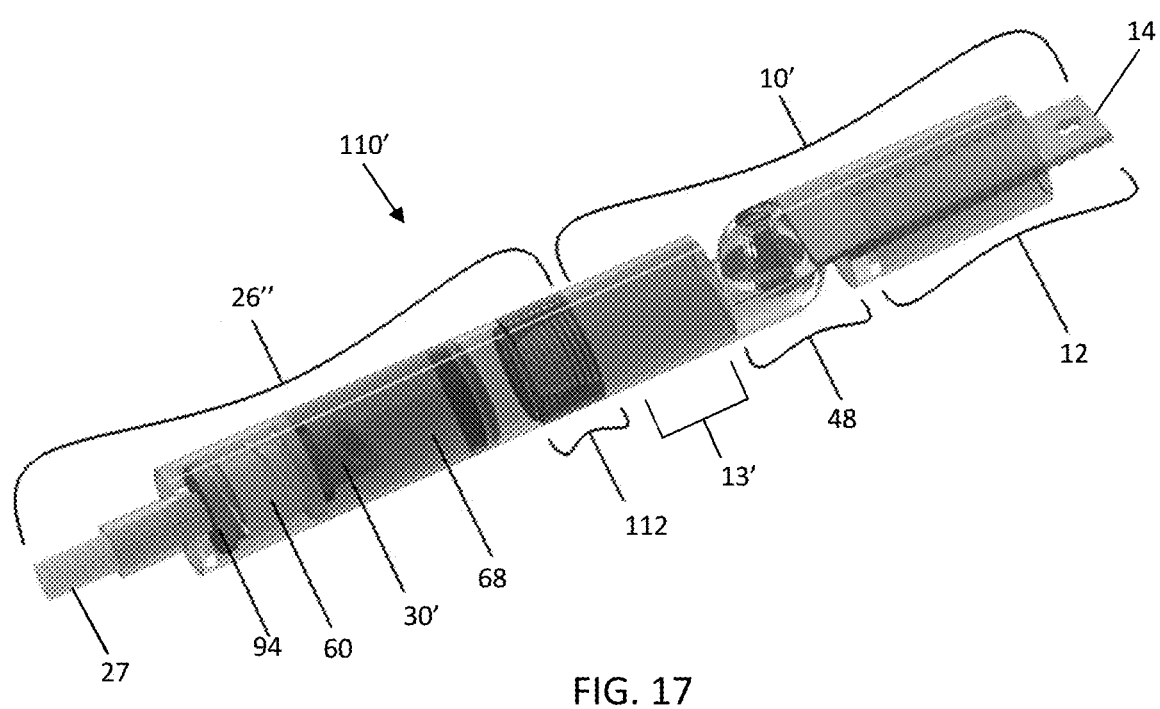

FIG. 17 depicts an embodiment of a fluid-delivery system having the fluid-delivery device of FIGS. 15A and 15B connected to an adapter.

DETAILED DESCRIPTION OF THE DRAWINGS

The present invention has utility as adapter to adapt a grasping instrument into a fluid-delivery device that can then deliver one or more fluids to tissue, organs, or parts thereof through a narrow orifice (e.g., port, sheath, trocar, tube, cannula, or natural cavity). In particular, the delivery of fluids may be used to mark tissue with a pigment, ink, or dye to aid in at least one of: the monitoring of movement of the marked tissue, organ, or part thereof; training or demonstrating an endoscopic procedure; and highlighting normal and abnormal tissues. The adapted grasping instrument may further be used to: deliver therapeutic agents to specific target tissues; deliver natural or synthetic glues to reinforce target tissue; deliver hemostatic agents to control bleeding surface; all of which refer to the application of fluid to tissue. The adapted grasping instrument may further be used to place radiopaque markers to facilitate and target post-surgical therapies. Further, the adapted grasping instrument may be used for non-medical applications where a gas, fluid, gel, or solid needs to be delivered to a target area under indirect visual conditions through various narrow orifices. The following description of various embodiments of the invention is not intended to limit the invention to those specific embodiments, but rather to enable any person skilled in the art to make and use this invention through exemplary aspects thereof.

It is to be understood that in instances where a range of values are provided that the range is intended to encompass not only the end point values of the range but also intermediate values of the range as explicitly being included within the range and varying by the last significant figure of that range. By way of example, a recited range of 1 to 4 is intended to include 1-2, 1-3, 2-4, 3-4, and 1-4.

As used herein, the term "fluid" refers to a liquid fluid, gas, gel, or a plurality of particulated solids that act like a fluid as a whole. In specific embodiments, the fluid is ink for marking tissues during endoscopic surgery. The term "grasping instrument" generally refers to any instrument capable of grasping a handle associated with the adapter as described below. In a specific embodiment, the grasping instrument is a pair of surgical forceps used in endoscopic surgery. The term "fluid-delivery device" refers to any device capable of marking an object or delivering fluid in/on an object such as a marker, a syringe, or a container having fluid therein.

With reference now to the drawings, and in particular FIGS. 1 through 10 thereof, examples of the instant adapter employing the principles and concepts of the present an adapter and generally designated by the reference number 10 will be described.

In general, the adapter 10 is preferably configured to attach to the jaws of most grasping instrument, and more specifically, most surgical endoscopic grasping instruments. The adapter 10 allows for the attachment of a fluid-delivery device to enable the delivery of a variety of materials, including, for example, pigments or other fluids that can be spread, injected, or imbedded on the surface or within tissues during any type of endoscopic surgery that utilizes hollow trocars, tubes, or cannulas inserted into any natural or created cavity in the body. Specific embodiments of the adapter 10 are further described below.

Referring particularly to FIGS. 1 through 4 a particular embodiment of the present adapter 10 is illustrated. The adapter 10 generally includes a proximal portion 12 and a distal portion 13. The proximal portion 12 includes a grasping handle 14 to be grasped by grasping instrument 16, and a collar 18 positioned about at least a portion of the grasping handle 14 to form a pair of openings (20, 22) therebetween. Each opening (20, 22) receives and encircles a jaw of the grasping instrument 16 to further stabilize and secure the adapter 10 to the grasping instrument 16. The distal portion 13 is disposed distal to the proximal portion 12. The distal portion 13 includes a chamber 24 to receive a fluid-delivery device 26 therein (as shown in FIG. 2). The chamber 24 includes an inner proximal end surface 28 having at least one of a cone 30 or a cylinder 32 projecting therefrom and towards a distal end of the chamber 24. The cone 30 or cylinder 32 makes contact with a proximal end surface 34 of the fluid-delivery device 26 when placed inside the chamber 24 such that when a pressure is applied against a distal end of the fluid-delivery device 26, fluid contents inside the fluid-delivery device 26 are expelled therefrom. The fluid-delivery device 26 may further include a tip 27 (e.g., a brush tip, an aperture/opening/hole, a threaded male tip, a needle) from which the fluid is expelled.

The adapter 10 can be easily and snugly attached to most grasping instruments 16 already in general use by way of the unique handle 14 and collar 18 docking mechanism. In some embodiments, the handle 14 is made of a compressible material where the handle 14 is compressed when the jaws of the grasping instrument are closed. The handle 14 may further include a hollow interior to further contribute to the compressibility of the handle 14. In a particular embodiment, the collar 18 is thin and flexible to snugly encircle the outer surface of the jaws to prevent the adapter 10 from being inadvertently dropped even when the grasping jaws are not completely closed on the handle 12. In some embodiments, each jaw of the grasping instrument 16 snugly fits into their corresponding openings (20, 22) between the handle 12 and collar 18 to form a press-fit interaction therebetween for further stability.

In particular embodiments, the collar 18 may be fixed into position relative to the handle 14 as shown in FIGS. 1 to 4. Here, the collar 18 encircles the handle 14, where opposing ends of the handle 12 attach to opposing regions of the collar 18 to form a first opening 20 situated on one side of the handle 14 and a second opening 22 situated on an opposing side of the handle 14. This requires zero adjustment of the collar 18 because the collar 18 is fixed in position. In another embodiment, the collar 18 is flexible and deployable. The collar 18 may initially be in a pre-deployed state, where the collar 18 is rolled or folded up to expose the handle 14. Then, after the jaws engage the handle 14, the collar 18 is unfolded or rolled over the jaws of the handle 14 to further secure the grasping instrument 16 to the adapter 10.

The adapter 10 may further include a middle portion 15 disposed between the proximal portion 12 and the distal portion 13. The middle portion 15 may have various functions as described below. The overall shape of the adapter 10 may by cylindrical, where the proximal portion 12, the distal portion 13, and the middle portion (if present), are connected in series and are each generally cylindrical in shape. However, it should be appreciated that the adapter 10 may come in a variety of forms or shape without deviating from the scope of the invention.

The distal portion 13 may be in the form of a chamber 24 to receive a fluid-delivery device 26 therein as shown in FIG. 2. The chamber 24 may include the inner proximal end surface 28, one or more side walls 29, and a distal open end. In some embodiments the chamber 24 is cylindrical having a single cylindrical side wall 29, while in other embodiments, the chamber 24 in non-cylindrical having two or more side walls 29. The fluid-delivery device 26 may be inserted into the chamber 24 via the distal open end of the chamber 24 and secured therein. The fluid-delivery device 26 may be secured using a fastening element such as a screw or other threaded mechanism near or at the inner proximal end surface 28 or by way of a plurality of clips 31 positioned along the length of the side walls 29. The fluid-delivery device 26 may be secured by way threads disposed along a portion of the length of the walls 29 of the chamber 24 that interlock with threads disposed on the fluid-delivery device 26.

In particular embodiments, the adapter 10 may be configured to overcome the positive pressure of the endoscopy environment and ensure smooth flow of fluid from the fluid-delivery device 26. The cone 30 projecting from the inner proximal end surface 28 of the chamber 24 may have a pointed end to penetrate the proximal end of the fluid-delivery device 26. The cone 30 may have a hollow interior that is in communication with a hollow interior of the handle 14 to form a central compressible reservoir therebetween. The central reservoir is activated by pressure exerted by the jaws of the grasping instrument 16. Compression by the jaws transmits a positive pressure through the central reservoir and into the fluid-delivery device 26 to expel the fluid contents therein. In another embodiment, the pressure may be transferred to the fluid-delivery device 26 by way of a hollow rigid tube disposed between the handle 14 and the cone 30, or the fluid-delivery device 26 may be integrated directly with a central reservoir. It should be appreciated, that in some embodiments, the cone 30 does not penetrate the fluid-delivery device 26 but rather applies the pressure exerted from the jaws onto the proximal end of the fluid-delivery device 26. In some embodiments, if a middle portion 15 is present, a hollow tube or other opening is present therein to form a middle region of the central reservoir. This allows the pressure generated at the handle 14 to flow through the middle portion 15, to the cone 30, and in or against the fluid-delivery device 26. It should be appreciated however that the fluid may be expelled from the tip 27 by applying pressure against the tip or other portion of the delivery device 26 without the need for the central reservoir.

With reference now to FIG. 5, the collar 18 may include one or more perforations (36, 38) to allow the adapter 10 to be easily detached from the grasping instrument 16 inside the operational cavity without having to remove the grasping instrument 16 and adapter 10 therefrom. The perforations (36, 38) may run along the length of the collar 18. In some embodiments, the perforations (36, 38) are oriented such that the angle between the longitudinal axis of the handle 14 and the axis of the perforations ranges from 0 to 90 degrees. The perforations (36, 38) are configured to tear when the grasping jaws are forcefully/quickly opened, thereby allowing the adapter 10 to detach freely from the grasping instrument 16. Thus, the user can easily remove the adapter 10 from the grasping instrument 16 if needed, and use the grasping instrument 16 for its original use without having to remove the grasping instrument from the surgical site. This is particularly advantageous for robotic procedures to minimize the removal and re-insertion of surgical instrument into and out of a surgical cavity.

FIG. 5 further depicts another embodiment of the adapter 10. The adapter 10 may further include an anchoring/retrieval mechanism for delayed removal and safety. The retrieval mechanism is configured to anchor and retrieve the adapter 10 if it has been removed, intentionally or unintentionally, from the grasping instrument 16. The retrieval mechanism may also be used for delayed removal of the adapter at the end of a surgical procedure to protect against the danger of inadvertent retention. In a particular embodiment, the retrieval mechanism is in the form of a cord 40 (e.g., suture, rope, twine, wire, or other string-like structure) firmly attached to the adapter 10. The cord 40 may be attached to an anchor 42 (e.g., an eyelet, a channel in the collar 18, or integrated directly with the collar 18) situated on the proximal portion 12 of the adapter 10. In some embodiments, the cord 40 is attached to the anchor with knots and a twisted or bent wire. In most surgical situations, a suture is used as the cord 40 where one end is attached to the anchor 42 and the opposing end is attached to a portion of the grasping instrument 16. The cord 40 is preferably of sufficient length so that the opposing end of the cord 40 is anchored to the grasping instrument 16 outside of the working space. The reason being, if the adapter 10 is used as a fluid-delivery device to mark tissues with a pigment or dye, the adapter 10 is often used at the beginning of the procedure and it may be inconvenient to remove the adapter 10 from the surgical site until the end of the procedure. Therefore, the user can use the grasping instrument 16 after the tissue is marked without the adapter 10 interfering with the remainder of the procedure. The retrieval mechanism is additionally advantageous to remind the user to remove the adapter 10 from the surgical site to ensure the adapter 10 is not left therein when the procedure is complete. In another embodiment, the cord 40 is advantageously made of conducting wire to transfer an electronic impulse to or from the adapter 10.

In specific embodiments, with reference to FIGS. 6 to 8, the adapter 10 includes one or more malleable support structures. Preferably, the adapter 10 is bendable to facilitate easy accessibility into uneven and/or non-horizontal intracorporeal regions. The bendability of the adapter 10 may be accomplished using different mechanisms as dictated by the unique situations in which the adapter 10 is used as further described. In one embodiment, as shown in FIG. 6, the malleable supports are a plurality of rods 44 (e.g., strips, wires, bars, tubes) made from a malleable material and integrated into the structure of the adapter 10. The rods 44 may be aligned along the longitudinal axis (proximal end to distal end) of the adapter 10 to impart rigidity to the adapter 10 and also permit the adapter 10 to bend when a lateral pressure is applied near the tip 27 of the fluid-delivery device 26 or on the distal portion 13 of the adapter 10. In some embodiments, the rods 26 extend along the entire length of the adapter 10 from the distal portion 12 to the proximal portion 13. The rods 44 may further make up a middle portion 15 of the adapter 10 to extend the overall length of the adapter 10 as shown in FIG. 6; however it should be appreciated that the adapter 10 may not include a middle portion 15 where the rods 44 simply extend along the lengths of the distal portion 12 and proximal portion 13. In addition, the number of the rods 44 may vary from one to several, and arranged at regular intervals around the circumference of the adapter 10.

In another embodiment, the malleable support structure is a spiral support 46 as shown in FIG. 7. The spiral support 46 may likewise be a strip or wire made of a malleable material to provide rigidity, yet bendability, to the adapter 10. The spiral support 46 may be combined with the rods 44 as described above. The spiral support 46 may be disposed along the length of the adapter 10. The spiral support 46 may further be disposed within the structure of the adapter 10, or on the outside of the adapter 10 as shown in FIG. 6. The spiral support 46 allows the proximal portion 13 to bend at least 90 degrees relative to the distal portion 12 without compromising or kinking any interior structures (e.g., central reservoir) of the adapter 10.

The malleable support structure may also be arranged in a diamond grid (similar to an arterial stent) positioned along the length and circumference of the adapter 10. This provides a malleable support structure that combines the rods 44 and the spiral support 46 into an integrated grid support structure that allows construction of a thinner outer structural wall (e.g., the thinness of the side walls 29 and thinness of the collar 18) of the adapter 10.

With reference now to FIG. 8, the adapter 10 may include a ratcheting hinge 48 to permit the proximal portion 12 to bend relative to the distal portion 13. The ratcheting hinge 48 may connect the proximal portion 12 to the distal portion 13 and therefore be part-of or make-up the middle portion 15 of the adapter 10. The ratcheting hinge 48 may allow the tip 27 to be angulated up to 90 degrees (in either direction for a total of 180 degree range) relative to the proximal portion 12. The tip 27 may be angulated by applying a gentle pressure against the tip 27 or distal portion 13 of the adapter 10 when the adapter is inside the working space/cavity. For example, the user can bend the tip 27 by pushing the distal portion 13 against an intracorporeal tissue or structure to apply pressure thereon. It should be appreciated, that the hinge 48 may be positioned near the center of the adapter 10 or closer to the proximal end or distal end of the adapter. In some embodiments, if the hinge 48 is located more towards the center of the adapter 10 and a central reservoir is desired between the handle 14 to the cone 30 as described above, a flexible hollow tube may be disposed across the hinge 28 to complete the central reservoir and allow the transfer of pressure from the handle 13 to the cone 30. In other embodiments, if the ratcheting hinge 28 is positioned closer to the proximal end of the adapter 10, then the central reservoir and pressure transfer may not be used. If the ratcheting hinge 28 is positioned closer to the distal end of the adapter 10, then the central reservoir may connect with the cone 30 directly as described above.

In a particular embodiment, with reference to FIG. 9, the adapter 10 includes a corrugated outer wall 50 to permit the adapter 10 to bend without compromising the internal structures (e.g., central reservoir). In cases where the length of the adapter 10 needs to be kept at a minimum, multiple circumferential corrugated ridges are integrated with/into the outer wall or shell structure of the adapter 10. The corrugated outer wall 50 or shell may surround the exterior of the proximal portion 12 and distal portion 13 of the adapter 10. In other embodiments, the corrugations are integrated directly into exterior portions of the collar 18 and side walls 29 of the chamber 24. If a middle portion 15 is present, then the corrugated outer wall 50 may further surround the exterior of the middle portion 15 or be integrated therein.

In a specific embodiment, the adapter 10 may include a replenishing mechanism to either replenish fluids inside the fluid-delivery device and/or provide a constant fluid flow out of the distal end of the adapter 10. The adapter 10 may include a port that is accessible on an exterior portion of the adapter 10. In one embodiment, the port is part-of the anchor 42. The port is in fluid communication with a fluid route (e.g., tube, channel) integrated inside the adapter 10. The fluid route may either: a) connect with the central reservoir between the handle 14 and cone 30 as described above, where fluid flows from the port, through the fluid route, into the central reservoir, and inside the fluid-delivery device 26; and/or b) extend into the chamber 24 and/or extend to the distal end of the chamber 24 to provide constant flow to the target site directly without the use of a fluid-delivery device 26. To provide the replenishing fluid, an external fluid source is connected to the port. The external fluid source may be present outside the working site/cavity and may be connected to the port by way of a hollow tube.

It should be appreciated, that the adapter 10 may be designed to accept a variety of interchangeable and purposely constructed devices that can be received inside the chamber 24 and used with the adapter 10. These "secondary devices" may vary in structure and function and may not necessarily need to be a fluid-delivery device 26.

In a particular embodiment, the adapter 10 may be used with an extendable grasper, which may be used for medical or non-medical use. The extendable grasper is constructed for use when the grasping instrument 16 are not suitable or unable to securely grip the adapter 10. The extendable grasper may be of a rigid and light material to provide a universal extension for introduction of the adapter 10 into any working space/cavity. The length of the extendable grasper is approximate in length that is appropriate for any particular procedure/application.

In a specific embodiment, with reference to FIG. 10, the adapter 10 may include a spring mechanism. The middle portion 15 of the adapter 10 may include a spring 52 and a platform 54. The spring 52 and platform 54 exerts pressure on the fluid-delivery device 26 as fluid is expelled therefrom. The fluid-delivery device 26 may be constructed with a corrugated container 26 to permit the device 26 to more easily compress and release fluid therefrom. The fluid-delivery device 26 may have ink therein to mark tissues during endoscopic surgery. The tip 27 may be a brush tip, which is unaffected by moisture, to deliver fluid to the tissue. In specific embodiments, the diameter of the adapter 10 is equal to or less than 7.8 mm. The length of the collar 18 may be 2.5 cm and the length of the spring 52 is 3.5 cm to 4 cm for a total length of 6 cm to 7 cm. The collar 18 may be bendable having corrugations. A 2.5 cm long collar 18 will therefore permit around 90 degrees of bending.

Adaptable for Use in Non-Endoscopic Procedures

The adapter 10 is easily adaptable for use on skin or in open surgical procedures by attaching a plastic or metal barrel (to act as an extension) with a unique and secure double prong docking mechanism that mimics the jaws of the grasping instrument 16. The prongs of the barrel likewise engaging the openings (20, 22) of the collar 18 to attach the adapter 10 to the barrel. A pressurizing ring may be pushed over the prongs to apply pressure thereto to grasp the handle 14 and secure the barrel to the adapter 10. The pressure replicates the pressure that is applied by the jaws of the grasping instrument 16. The barrel is configured to be held by a user and is of ergonomic design.

Construction

The adapter 10 is sterile and non-toxic. The method of sterilization may vary depending on the materials of the adapter 10. In the event the adapter 10 is made of different materials, then the adapter 10 may be assemblable, where each part may be sterilized individually and re-assembled.

The size of the adapter 10 is preferably ultra-slim to be deployable in ports as small as 5 millimeters (mm) in diameter if needed. The adapter 10 is preferably available in multiple options of length, diameter, flexibility, and application so as to allow a multitude of materials to be delivered via a fluid-delivery device 26 or other secondary device.

The adapter 10 and/or parts thereof may be constructed of a polymeric material such as silicone or siliconized rubber. In other embodiments, the adapter 10 or parts thereof are made of a metal. The construction material is primarily dependent on the unique characteristics of the environment in which the adapter 10 is used. For example, when rigidity and resistance to lateral compressibility is required, a metallic structure may be more beneficial. In another example, when the adapter 10 is used with electrocautery, a more non-conductive construction material is desirable.

The length of the adapter 10 preferably ranges between 3 and 10 centimeters (cm) depending upon the specific requirements of the procedure. For instance, a smaller working space/cavity (e.g., arthroscopic joint surgery) requires a very compact adapter 10, whereas laparoscopic surgery in the abdomen can accommodate a longer adapter 10. The diameter of the adapter 10 preferably ranges between 2.8 mm and 1.50 cm. The most common diameter foreseen is a diameter ranging from approximately 4.0 to 5.0 mm to approximately 9.5 to 10 mm (4.0 mm to 10 mm). More particularly, the diameter of the adapters 10 are preferably sized to accommodate all sizes of endoscopic cannulas, where the currently available endoscopic surgery cannulas have diameters of 3 mm, 5 mm, 10 mm, and larger sizes.

The depth of the handle 14 and/or openings (20, 22) may be determined based on the length of the jaws of the grasping instrument 16. Many commonly used grasping instrument have jaws with a length ranging from 1 cm to 4 cm. Generally, larger grasping instrument 16 need a deeper handle 14 and/or openings (20, 22) to ensure a firmer grasp of the adapter 10 to the grasping instrument 16.

The handle 14 may come in a variety of forms. In some embodiments, the handle 14 is narrow at the apex (most proximal end) and tapers outward distally where the distal end of the handle 14 is thicker than the apex as shown in FIG. 1. In other embodiments, the handle 14 is not tapered and may be shaped in another form (e.g., straight as shown in FIGS. 8 and 9). The handle 14 may be made of a compressible or soft material to increase the grip of the grasping instrument 16 thereon. The depth of the handle 14 runs proximal to distal (longitudinally), while the width of the handle 14 runs transversely thereto. Opposing transverse ends of the handle 14 are attached to opposing portions of the collar 18 as described above to form a first opening 20 on a first side of the handle 14 and a second opening 22 on an opposing side the handle 14.

The extendable grasper for use with the adapter 10 when the grasping instrument 16 is inadequate is preferably constructed of three tapered conical cylinders of diminishing diameter and almost equal in length, with each cylinder placed within another. The cylinders may be collapsible within each other. The length of each cylinder may be approximately 5 cm to 12 cm, and when the three are fully extended, the length is about 18 cm to 30 cm. The cylinders may be constructed of a strong, rigid, and light metal and/or polymeric material. The apex of the smallest cylinder is the tip of the extender, and the base of the largest cylinder is fitted with an ergonomic soft gripping surface. When the extendable grasper is extended, the base of the smaller cylinders are firmly gripped by grooves on the inner surface of the apex of the larger cylinders. The tip of the extendable grasper bears two prongs, which fit snugly into the openings (20, 22). A pressure ring may be pushed over the prongs to secure the prongs to the handle 14 and approximate the pressure created by jaws of the grasping instrument 16. The pressure ring may be constructed of a flexible but non-elastic material.

Function

The following is an example of a method for using the adapter for a grasping instrument adapter 10 as described above.

The adapter 10 is removed from sterile packaging and inspected for integrity.

Next, a grasping instrument 16 is secured to the adapter 10. If the collar 18 is fixed relative to the handle 14, then the jaws of the grasping instrument 16 are inserted into the openings (20, 22) and clamped down on the handle 14. Lubrication may be used to more easily slip the jaws into the opening (20, 22). If the collar 18 is deployable, then the jaws are first clamped down onto grasping the handle 14 and the collar 18 is then flipped or rolled over the jaws.

Once secured, the adapter 10 may be anchored to the instrument 16 with an anchoring mechanism as described with reference to FIG. 5. If the adapter 10 is not pre-fitted with an anchoring mechanism, then a cord 40 is securely fastened between the instrument 16 and an anchor 42. More specifically, the cord 40 may be tied to an eyelet of the anchor 42.

Then, a fluid-delivery device 26 or secondary device is inserted into the chamber 24 and secured therein (e.g., with a threaded mechanism between the proximal end of the delivery device 26 and the proximal end surface 28 of the chamber 24). The fluid-delivery device 26 may likewise be attached/connected to the adapter 10 by other mechanism as described below with reference to FIGS. 16 and 17. The grasping instrument 16 and adapter 10 are now ready for use.

The grasping instrument 16 secured to the adapter 10 is inserted into a working space/cavity. The fluid-delivery device 26 or adapter 10 may have orientation markings to help the user identify the orientation of the device 26 when seen on a camera inside a cavity. The tip 27 is approximated to the surface of the target tissue with light pressure. A pressure is applied to the fluid-delivery device 26 just proximal to the tip 27 on its posterior or inferior surface to expel fluid from the tip 27. After completing the task (e.g., marking tissue), the instrument 16 can be detached from the adapter 10 by forcefully opening the grasping jaws, tearing the collar 18, and letting the adapter 10 drop into the working space/cavity, held only by the anchoring mechanism. In case the adapter 10 needs to be used later in the procedure, then the perforations (36, 38) may not need to be torn where the jaws of the grasping instrument 16 may be released from the handle 14 without disrupting the collar 18.

If the adapter 10 is detached from the collar 18 and inside the working space, the adapter 10 can be removed from the working space by grasping the adapter 10 at the handle 14 or by traction on the anchoring mechanism. Conversely, the adapter 10 may be removed without detaching the adapter 10 from the instrument 16 by withdrawing the instrument 16 with the adapter 10 attached thereto and manually detaching the adapter 10 from the instrument 16.

Fluid-Delivery Device Examples

Example 1

With reference to FIGS. 11 to 13D, particular embodiments of a fluid-delivery device 26 are shown. The fluid-delivery device 26 may include a fluid dispensing assembly 56 and a fluid housing assembly 58. The fluid dispensing assembly 56 generally includes a tip 27, a tip saturator 60 proximally adjacent to the tip 27, a secondary flow regulator 62 proximally adjacent to the tip saturator 60, a primary flow regulator 64 proximally adjacent to the secondary flow regulator 62, and a receptacle 66 proximally adjacent to the primary flow regulator 64. The fluid housing assembly 58 generally includes a fluid cartridge 68 having fluid contents therein, and a compressible section 70 proximally adjacent to the fluid cartridge 68. The fluid dispensing assembly 56 and fluid housing assembly 58 are removably connectable, where the fluid housing assembly 58 can provide fluid contents to the tip 27, yet replaceable when the fluid contents in the cartridge 68 are depleted.

The dispensing assembly 56 and the housing assembly 58 may be connected where a portion of the housing assembly 58 is received in the receptacle 66 of the fluid dispensing assembly 58. To secure the two assemblies together, the fluid housing assembly 58 may include threads 72 extending along at least a portion of an exterior surface of the housing assembly 58 that interlock with corresponding threads 74 disposed along at least a portion of an interior surface of the receptacle 66. This may be akin to a nut and bolt, where the receptacle 66 acts as the nut and the housing assembly 58 acts as the bolt. In some embodiments, the interior of the receptacle 66 and the exterior portion of the housing assembly 58 to be received therein are cylindrical like a nut and bolt. It should be appreciated that other connection mechanisms between the dispensing assembly 58 and the housing assembly 60 are possible including a press-fit connection or with the use of other fastening mechanisms (e.g., clamps, clasps, set screws).

The dispensing assembly 58 and the housing assembly 60 are connected such that when the compression section 70 is compressed, pressure is exerted on the fluid cartridge 68 causing the fluid contents therein to flow through the primary flow regulator 64 and then through the secondary flow regulator 66 and into the tip saturator 60, which provides the fluid contents to the tip that can then mark objects with the fluid contents. FIG. 11 depicts the dispensing assembly 58 and the housing assembly 60 disconnected, and FIG. 12 depicts the dispensing assembly 58, housing assembly 60, and adapter 10 all connected together.

With reference to FIGS. 13A-13D, embodiments of the primary flow regulator 64 and the secondary flow regulator 62 are shown in more detail. The primary flow regulator 64 and the secondary flow regulator 62 are generally configured to control the flow of fluid to the tip saturator 60. The primary flow regulator 64 includes a first regulation plate 76, and a pipe 78 extending proximally therefrom. The first regulation plate 76 and pipe 78 have a primary orifice 80 therethrough to permit fluid flow from the cartridge 68, through the pipe 78, and past the regulation plate 76. The pipe 78 may have a pipe tip at the pipe's proximal end to pierce through the cartridge 68 to gain access to the fluid contents therein. The secondary flow regulator 62 includes a reservoir 82 and a second regulation plate 84. The reservoir 82 is distally adjacent to the first regulation plate 76 to collect fluid therein after the fluid passes through the primary orifice 80. The second regulation plate 84 is located at a distal end of the reservoir 82. The second regulation plate 84 includes a plurality of secondary orifices 86 (four secondary orifices 86 are shown in FIGS. 13A and 13C) to permit fluid to flow from the reservoir 82 to the tip saturator 60. Note, the direction of fluid flow is depicted in FIG. 13 by the dotted arrows.

The tip saturator 60 is preferably made of an absorbent and compressible material (e.g., polymeric foam, a sponge, textiles) that can be saturated with the fluid contents from the cartridge 68. The tip saturator 60 enables a user to saturate the tip 27 with the fluid contents only when desired, in an effort to reduce fluid leaks and dripping. For example, a user can press the tip 27 against a surface causing fluid to expel from the cartridge 68, through the regulators (62, 64), and saturate the tip saturator 60. A proximal end of the tip 27 may be in communication with the tip saturator 60, either directly or indirectly (e.g., a small port or hole between a distal end of the tip saturator 60 and the proximal end of the tip 27), to wet the tip 27 or provide the fluid contents to a distal end of the tip 27.

Referring back to the compression section 70, in a particular embodiment, the compression section may include the spring 52 and platform 54 as shown in FIG. 10. In other embodiments, the compression section 70 includes a compressible material such as an elastic and/or compressible polymer or textile. Finally, in a particular embodiment, with reference to FIG. 12, the compression section 70 may include a hole 88 to equalize the pressure that may build during compression. In addition, if there is an air-tight seal between the compression section 70 and the walls of the chamber 24, the chamber 24 may include a hole in communication with the hole 88 of the compression section 70 to permit the pressure to equalize.

Example 2

With reference to FIGS. 14A to 14B, a particular embodiment of a fluid-delivery device 26' is shown, where FIG. 14A depicts an exploded view of the fluid-delivery device 26' and FIG. 14B depicts an assembled view of the fluid-delivery device 26'. The fluid-delivery device 26' may include an outer casing 90 and fluid deliver assembly 92 that fits inside the outer casing 90. The outer casing 90 may be in the form of a cylinder having a proximal open end and a distal open tip end 91, where the proximal open end has an open diameter greater than the distal open tip end 91.

The fluid-delivery assembly 92 generally includes a tip 27, a seal 94 proximal to the tip 27, a tip saturator 60 proximal to the seal 94, a spring 96 surrounding the tip saturator 60 and applying pressure against the seal 94 to form a leak-proof seal with the tip 27, a flow regulator 98 proximal to the tip saturator 60, a fluid reservoir 100 proximal to the flow regulator 98 to house fluid that is dispensed by the tip 27, a first connection member 102 disposed at a proximal end of the fluid reservoir 100 to connect the fluid-delivery assembly 92 with the outer casing 90, and a second connection member 104 proximal to the first connection member 102 to connect with the adapter 10. The tip 27 is configured to mark tissue as described above and may illustratively include a brush tip, an aperture/opening/hole, a threaded male tip, or a needle. The seal 94 is configured to form a seal between the tip saturator 60 and the tip 27 and may include a rubber seal for example. A portion of the seal 94 may include one or more openings, conduits, or a transfer medium to permit fluid to wet the tip 27 from the tip saturator 60. The tip saturator 60 may include for example a sponge, polymeric foam, textiles, or be made of other absorbent materials to transfer fluid from the fluid reservoir 58' to the tip 27. The spring 96 is configured to assist the tip 27 to form a leak-proof seal by applying pressure against the seal 94. The spring 96 wraps around the tip saturator 60 with a first end of the spring applying pressure against the seal 94 and the opposing end of the spring 96 applying pressure against the flow regulator 98. As such, the diameter of the tip saturator 60 may be less than a diameter of the flow regulator 98 and the seal 94. The flow regulator 98 may be of the same or a similar design to the flow regulators (62 and/or 64) as described above with reference to FIGS. 11 to 13D. The fluid reservoir 100 may include a central support 106 and an outer open region 107 radial to the central support 106. The central support 106 is configured to form a link between the flow regulator 98 and the first and/or second connection members (102, 104). The central support 106 may be in the form of a cylinder that traverses along a central longitudinal axis of the fluid-delivery assembly 92 and attaches/integrates/connects the flow regulator 98 with the connection members (102 and/or 104). The outer open region 107 of the fluid reservoir 100 extends radially about the central support 106 and is configured to house fluid, where a seal between the outer open region 107 and the outer casing 90 is formed when the fluid-delivery assembly 92 is assembled inside the outer casing 90. The first connection member 102 is configured to attach/connect with the outer casing 90. The outer casing may include a connection member 108 located at a proximal end of the outer casing 90 that attaches/connects with the first connection member 102 of the fluid-delivery assembly 92. The connection may be formed with a fastening element such as inner and outer screw threads, clasp, snap buttons, a bayonet joint, a clip or other connection mechanisms such as a press-fit or adhesives. The second connection member 104 is configured to attach/connect with the adapter 10. Likewise, the connection may be formed with a fastening element such as inner and outer screw threads, clasp, snap buttons, a bayonet joint, a clip or other connection mechanisms such as a press-fit or adhesives. FIG. 14B depicts the fluid-delivery device 26' in an assembled state. Here, it can be seen that the tip 27 of the fluid-delivery assembly 92 extends or protrudes through the distal open tip end 91 of the outer casing 90, and the first connection member 102 is threaded onto the connection member 108 of the outer casing 90.

Example 3

With reference to FIGS. 15A and 15B, a specific embodiment of a fluid-delivery device 26" is shown, where FIG. 15A is an exploded view of the fluid-delivery device 26" and FIG. 15B is an assembled view of the fluid-delivery device 26". The fluid-delivery device 26" generally includes an outer casing 90 and a fluid-delivery assembly 92' that fits inside the outer casing 90. The outer casing 90 may be in the form of a cylinder having a proximal open end to receive the fluid-delivery assembly 92', and a distal open tip end 91 to receive a tip 27 of the fluid-delivery assembly 92'. The proximal open end may have an open diameter greater than the distal open tip end 91. The outer casing 90 further includes a connection member 108 to attach/connect with an adapter 10.

The fluid-delivery assembly 92' generally includes a tip 27, a seal 94 proximal to the tip 27, a tip saturator 60 proximal to the seal 94, a spring 96 surrounding the tip saturator 60 and applying pressure against the seal 94 to form a leak-proof seal with the tip 27, and a flow regulator 98 proximal to the tip saturator 60, a piercer 30' proximal to the flow regulator 98. The tip 27 is configured to mark tissue as described above and may illustratively include a brush tip, an aperture/opening/hole, a threaded male tip, or a needle. The seal 94 is configured to form a seal between the tip saturator 60 and the tip 27 and may include a rubber seal for example. A portion of the seal 94 may include one or more openings, conduits, or a transfer medium to permit fluid to wet the tip 27 from the tip saturator 60. The tip saturator 60 may include for example a sponge, textiles, or be made of other absorbent materials to transfer fluid from the fluid reservoir 58' to the tip 27. The spring 96 is configured to assist the tip 27 to form a leak-proof seal by applying pressure against the seal 94. The spring 96 wraps around the tip saturator 60 with a first end of the spring applying pressure against the seal 94 and the opposing end of the spring 96 applying pressure against the flow regulator 98. As such, the diameter of the tip saturator 60 may be less than an overall diameter of the flow regulator 98 and the seal 94. The flow regulator 98 may be of the same or a similar design to the flow regulators (62 and/or 64) as described above with reference to FIGS. 11 to 13D. However, it should be appreciated that any of the flow regulators described herein may be a simple hole, channel, opening, or aperture. The piercer 30' is configured to pierce the contents of a fluid cartridge 68 when the fluid cartridge 68 is received inside the receptacle 66. The piercer 30' may be for example a cone, a needle, a beveled projection, or other mechanism capable of piercing the fluid cartridge 68. The piercer 30' may extend proximally from the flow regulator 98 and have a hollow interior to permit fluid to flow from the cartridge 68 to the tip saturator 60. The piercer 30' may extend proximally along a central longitudinal axis from the flow regulator 98. In some embodiment, the piercer 30' act as a fluid regulator where the hole or channel through the piercer 30' regulates flow to the tip saturator 60. In other embodiments, the flow regulator 98 is a plate having a hole or channel with the same as dimensions as the piercer 30' to act as a conduit between the cartridge 68 and the tip saturator 60. The cartridge 68 houses fluid therein and at least a portion of the distal end of the cartridge 68 is piercable by the piercer 30'.

Fluid-Delivery System Examples

Example 1

With reference to FIG. 16, an embodiment of a fluid-delivery system 110 is shown. The fluid-delivery system 110 generally includes an adapter 10' assembled with the fluid-delivery device 26' as described with reference to FIGS. 14A and 14B. The adapter 10' generally includes a proximal portion 12 and a distal portion 13'. The proximal portion 12 includes a grasping handle 14 to be grasped by a grasping instrument 16, and a collar 18 (shown in FIGS. 1-3) positioned about at least a portion of the grasping handle 14 to form a pair of openings (20, 22) therebetween as described above. The distal portion 13' includes a connection member at a distal end of the distal portion 13' to attach/connect with the second connection member 104 of the adapter 92. The connection may be formed with a fastening element such as inner and outer screw threads, clasp, snap buttons, a bayonet joint, a clip or other connection mechanisms such as a press-fit or adhesives. The adapter 10' may further include a hinge 48 between the proximal portion 12 and the distal portion 13'. The hinge 48 may be a ratcheting hinge as describe above or may be any other hinge mechanism (e.g., a pivot pin, a rotational joint, a spherical joint, etc.) that permits the distal portion 13' to pivot or rotate relative to the proximal portion 12. It should be appreciated that other mechanism to permit the distal portion 14 to move relative to the proximal portion 14 may be used such as the mechanisms described with reference to FIGS. 6 to 9. The fluid-delivery device 26' includes the components as described above with reference to FIGS. 14A and 14B. FIG. 16 depicts the fluid-delivery device 26' assembled with the adapter 10' by way of a threaded connection between the connection member at the distal end of the distal portion and the second connection member 104 of the fluid-delivery device 26' as shown at 112.

Example 2

With reference to FIG. 17, an embodiment of a fluid-delivery system 110' is shown. The fluid-delivery system 110' generally includes an adapter 10' assembled with the fluid-delivery device 26" as described with reference to FIGS. 15A and 15B. The adapter 10' generally includes a proximal portion 12 and a distal portion 13'. The proximal portion 12 includes a grasping handle 14 to be grasped by a grasping instrument 16, and a collar 18 (shown in FIGS. 1-3) positioned about at least a portion of the grasping handle 14 to form a pair of openings (20, 22) therebetween as described above. The distal portion 13' includes a connection member (e.g., threads, a smooth surface for a press-fit connection) at a distal end of the distal portion 13' to attach/connect with the second connection member 104 of the adapter 92. The connection may be formed with a fastening element such as inner and outer screw threads, clasp, snap buttons, a bayonet joint, a clip or other connection mechanisms such as a press-fit or adhesives. The adapter 10' may further include a hinge 48 between the proximal portion 12 and the distal portion 13'. The hinge 48 may be a ratcheting hinge as describe above or any other hinge mechanism (e.g., a pivot pin, a rotational joint, a spherical joint, etc.) that permits the distal portion 13' to pivot or rotate relative to the proximal portion 12. It should be appreciated that other mechanism to permit the distal portion 14 to move relative to the proximal portion 14 may be used such as the mechanisms described with reference to FIGS. 6 to 9. The fluid-delivery device 26' includes the components as described above with reference to FIGS. 15A and 15B. FIG. 17 depicts the fluid-delivery device 26' assembled with the adapter 10' at 112, and a cartridge 68 inside the outer casing 90 of the fluid-delivery device 26".

Other Embodiments

While at least one exemplary embodiment has been presented in the foregoing detail description, it should be appreciated that a vast number of variations exist. It should also be appreciated that the exemplary embodiment or exemplary embodiments are only examples, and are not intended to limit the scope, applicability, or configuration of the described embodiments in any way. It should be understood that various changes may be made in the function and arrangement of elements without departing from the scope as set forth in the appended claims and the legal equivalents thereof.

What is claimed is:
1. A fluid-delivery system for applying fluid to tissue, comprising:
    an adapter configured to connect with a grasping instrument; and
    a fluid-delivery device configured to connect with the adapter and apply the fluid to the tissue;
    wherein said adapter comprises:
        a proximal portion having a grasping handle configured to be grasped by the grasping instrument which has a pair of jaws; and a distal portion distal to the proximal portion, wherein the distal portion comprises a chamber having a first dimension configured to couple with the fluid-delivery device; and wherein said fluid-delivery device comprises:
a tip at a distal end of the fluid-delivery device to apply the fluid to the tissue;
a tip saturator proximally adjacent to the tip to supply the fluid to the tip;
a flow regulator proximally adjacent to the tip saturator;
a fluid housing proximal to the flow regulator, wherein the fluid housing is configured to house a fluid cartridge containing the fluid which is appliable to the tissue; and
a proximal end proximal to the fluid housing, wherein the proximal end has a second dimension smaller than the first dimension of the chamber in order for the proximal end to fit inside the chamber of the adapter.

2. The fluid-delivery system of claim 1 wherein the proximal portion of the adapter further comprises a collar positioned about at least a portion of the grasping handle such that a pair of openings are formed between the grasping handle and the collar, wherein each opening of the pair of openings is configured to receive and encircle a jaw of the pair of jaws of the grasping instrument to further stabilize and secure the adapter to the grasping instrument.

3. The fluid-delivery system of claim 2 wherein the collar of the adapter further comprises perforations such that when the jaws of the grasping instrument are forcefully opened, the perforations tear to release the jaws from the adapter.

4. The fluid-delivery system of claim 2 wherein the adapter further comprises an anchoring mechanism comprised of a tether attached to an anchor, wherein the anchor is attached to at least one of the grasping handle or the collar and the tether is configured to attach to the grasping instrument.

5. The fluid-delivery system of claim 2 wherein the adapter further comprises an adjustment mechanism disposed between the proximal portion and the distal portion to permit the distal portion to move relative to the proximal portion.

6. The fluid-delivery system of claim 5 wherein the adjustment mechanism is at least one of a hinge or one or more malleable support structures.

7. The fluid-delivery system of claim 5 wherein the adjustment mechanism is configured to permit the distal portion to rotate at least 10 degrees relative to the proximal portion.

8. The fluid-delivery system of claim 1 wherein the proximal end of the fluid-delivery device is at least one of: a) a smooth surface for a press-fit connection inside the chamber; b) threads to form an interlocking connection inside the chamber, or c) a cylindrical body to be received and secured inside the chamber.

9. The fluid-delivery system of claim 1 wherein said chamber comprises an inner proximal end surface that makes contact with a proximal end surface of the fluid-delivery device when the fluid-delivery device is placed inside the chamber such that when a pressure is applied against the tip of the fluid-delivery device, the fluid inside the fluid housing is expelled from the tip.

10. The fluid-delivery system of claim 1 wherein the tip of the fluid-delivery device is a brush tip.

11. The fluid-delivery system of claim 1 wherein the fluid cartridge is a disposable fluid cartridge, and wherein the fluid-delivery device further comprises a piercer extending proximally from the flow regulator to pierce at least a portion of the disposable fluid cartridge to access the fluid stored in the disposable fluid cartridge.

12. The fluid-delivery system of claim 11 wherein the fluid-delivery device further comprises an outer casing that encloses the tip saturator, the flow regulator, the piercer, and the fluid cartridge.

13. The fluid-delivery system of claim 1 wherein the fluid-delivery device further comprises an outer casing that encloses the tip saturator, the flow regulator, and the fluid housing when assembled in the outer casing, wherein the fluid housing further comprises:
a central support traversing along a central longitudinal axis of the fluid-delivery device to link the flow regulator with the proximal end of the fluid-delivery device; and
an outer open region extending radially about the central support, wherein a seal is formed between the outer open region and the outer casing to permit the fluid to be stored in the outer open region of the fluid housing.

14. The fluid-delivery system of claim 1 wherein the first dimension of the chamber is either a width of the chamber or a diameter of the chamber, and wherein the second dimension of the proximal end of the fluid-delivery device is either a width of the proximal end of the fluid delivery device or a diameter of the proximal end of the fluid delivery device.

15. The fluid-delivery system of claim 1 wherein the entirety of the fluid-delivery device is distal to the proximal portion of the adapter when the fluid-delivery device is coupled to the adapter.

16. An adapter configured to connect with a grasping instrument and a fluid-delivery device, the adapter comprising:
a proximal portion having a grasping handle and a collar positioned about at least a portion of the grasping handle such that a pair of openings are formed between the grasping handle and the collar, wherein said grasping handle is configured to be grasped by the grasping instrument which has a pair of jaws, and wherein each of said openings of the pair of openings is configured to receive and encircle a jaw of the pair of jaws of the grasping instrument to further stabilize and secure the adapter to the grasping instrument;
a distal portion distal to the proximal portion, wherein the distal portion comprises a chamber having a first dimension configured to couple to a proximal end of the fluid-delivery device, wherein the first dimension is larger than a second dimension of the proximal end of the fluid-delivery device in order for the proximal end of the fluid-delivery device to fit inside the chamber; and
an adjustment mechanism disposed between the proximal portion and the distal portion to permit the distal portion to move relative to the proximal portion, wherein the adjustment mechanism is at least one of a hinge or one or more malleable support structures.

17. The adapter of claim 16 wherein the collar of the adapter further comprises perforations such that when the jaws of the grasping instrument are forcefully opened, the perforations tear to release the jaws from the adapter.

18. The adapter of claim 16 wherein the first dimension of the chamber is either a width of the chamber or a diameter of the chamber, and wherein the second dimension of the proximal end of the fluid-delivery device is either a width of the proximal end of the fluid delivery device or a diameter of the proximal end of the fluid delivery device.

19. The adapter of claim 16 wherein the adjustment mechanism is configured to permit the distal portion to rotate at least 10 degrees relative to the proximal portion.

\* \* \* \* \*